United States Patent
Mohammadi et al.

(10) Patent No.: US 11,147,502 B2
(45) Date of Patent: Oct. 19, 2021

(54) SIGNAL TRIMMING AND FALSE POSITIVE REDUCTION OF POST-SEGMENTATION SWALLOWING ACCELEROMETRY DATA

(71) Applicant: HOLLAND BLOORVIEW KIDS REHABILITATION HOSPITAL, Toronto (CA)

(72) Inventors: Helia Mohammadi, Toronto (CA); Tom Chau, Toronto (CA)

(73) Assignee: Holland Bloorview Kids Rehabilitation Hospital, Toronto (CA)

( * ) Notice: Subject to any disclaimer, the term of this patent is extended or adjusted under 35 U.S.C. 154(b) by 424 days.

(21) Appl. No.: 16/074,577

(22) PCT Filed: Feb. 9, 2017

(86) PCT No.: PCT/IB2017/000183
§ 371 (c)(1),
(2) Date: Aug. 1, 2018

(87) PCT Pub. No.: WO2017/137844
PCT Pub. Date: Aug. 17, 2017

(65) Prior Publication Data
US 2019/0038208 A1 Feb. 7, 2019

Related U.S. Application Data

(60) Provisional application No. 62/292,995, filed on Feb. 9, 2016.

(51) Int. Cl.
*A61B 5/00* (2006.01)
*G16H 50/20* (2018.01)
*A61B 7/00* (2006.01)

(52) U.S. Cl.
CPC .......... *A61B 5/4205* (2013.01); *A61B 5/7203* (2013.01); *A61B 5/7282* (2013.01);
(Continued)

(58) Field of Classification Search
None
See application file for complete search history.

(56) References Cited

U.S. PATENT DOCUMENTS

2005/0283096 A1* 12/2005 Chau .................... A61B 5/6822
600/593
2008/0269646 A1 10/2008 Chau et al.
(Continued)

FOREIGN PATENT DOCUMENTS

WO 2013086615 6/2013

OTHER PUBLICATIONS

Hanna, Master Thesis "Investigating the Correlation between Swallow Accelerometry Signal Parameters and Anthropometric and Demographic Characteristics of Healthy Adults" Clinical Engineering Department—Institute of Biornaterials and Biomedical Engineering University of Toronto, 2008, 75 pages.
(Continued)

*Primary Examiner* — Matthew Kremer
(74) *Attorney, Agent, or Firm* — K&L Gates LLP (57) ABSTRACT

A method for quantifying swallowing function can include subjecting swallowing segments and non-swallowing segments of vibrational data to processing selected from the group consisting of adaptive trimming, false positive reduction, and a combination thereof. Preferably the vibrational data represents swallowing activity, is from a sensor positioned on the throat of a patient, and is associated with at least one axis selected from the group consisting of an anterior-posterior axis and a superior-inferior axis. Preferably a processing module operatively connected to the sensor performs the processing of the swallowing segments and the non-swallowing segments of the vibrational data. A device comprising a processing module and a sensor such as (Continued)

a single-axis accelerometer or a dual axis accelerometer can perform one or more steps of the method.

14 Claims, 8 Drawing Sheets

(52) U.S. Cl.
CPC ............ *G16H 50/20* (2018.01); *A61B 5/6822* (2013.01); *A61B 7/008* (2013.01); *A61B 2562/0204* (2013.01); *A61B 2562/0219* (2013.01)

(56) References Cited

U.S. PATENT DOCUMENTS

2009/0326871 A1* 12/2009 Watson .............. G06K 9/00516
  702/191

2011/0263999 A1* 10/2011 Carlson .................. A61N 2/006
  600/544

OTHER PUBLICATIONS

Sejdic et al. "Classification of Penetration-Aspiration Versus Healthy Swallows Using Dual-Axis Swallowing Accelerometry Signals in Dysphagic Subjects" IEEE Transactions on Biomedical Engineering, Jul. 2013, vol. 60, No. 7, pp. 1859-1866.

Damouras et al. "An Online Swallow Detection Algorithm Based on the Quadratic Variation of Dual-Axis Accelerometry" IEEE Transactions on Signal Processing, Jun. 2010, vol. 58, No. 6, pp. 3352-3359.

Mohammadi et al. "Post-Segmentation Swallowing Accelerometry Signal Trimming and False Positive Reduction" IEEE Signal Processing Letters, Sep. 2016, vol. 23, No. 9, pp. 1221-1225.

* cited by examiner

Estimation of $\Lambda^{AP}$ and $\Lambda^{SI}$ scalars

| Approach | $\Lambda^{AP}$ | $\Lambda^{SI}$ | TP | FP | FN | TP change (%) | FP change (%) | Recall | Precision | F |
|---|---|---|---|---|---|---|---|---|---|---|
| Existing | - | - | 1118 | 226 | 125 | - | - | 89.94 | 83.18 | 86.43 |
| mean | 0.8607 | 0.83776 | 704 | 9 | 539 | -37.03 | -96.02 | 56.64 | 98.74 | 71.99 |
| mean-std | 0.50967 | 0.56404 | 834 | 21 | 409 | -25.4 | -90.71 | 67.1 | 97.54 | 79.51 |
| mean-2xstd | 0.33865 | 0.29031 | 981 | 74 | 262 | -12.25 | -67.26 | 78.92 | 92.99 | 85.38 |
| MaxED (β.95) | 0.022297 | 0.07779 | 1113 | 216 | 130 | -0.45 | -4.42 | 89.54 | 83.75 | 86.55 |
| MaxED (β.9,.8) | 0.064121 | 0.07779 | 1113 | 206 | 130 | -0.45 | -8.85 | 89.54 | 84.38 | 86.88 |
| MaxED (β.75-.7) | 0.079054 | 0.07779 | 1113 | 200 | 130 | -0.45 | -11.5 | 89.54 | 84.77 | 87.09 |
| MaxED (β.65-.45) | 0.18512 | 0.07779 | 1079 | 163 | 164 | -3.49 | -27.88 | 86.81 | 86.88 | 86.84 |
| MaxED (β.4-.2) | 0.3168 | 0.07779 | 1040 | 115 | 203 | -6.98 | -49.12 | 83.67 | 90.04 | 86.74 |
| MaxED (β.15) | 0.3168 | 0.23489 | 1009 | 92 | 234 | -9.75 | -59.29 | 81.17 | 91.64 | 86.09 |
| MaxED (β.1) | 0.45828 | 0.32642 | 942 | 54 | 301 | -15.74 | -76.11 | 75.79 | 94.58 | 84.14 |
| MaxED (β0.05) | 0.67232 | 0.38375 | 865 | 23 | 378 | -22.63 | -89.82 | 69.59 | 97.41 | 81.18 |

Fig. 7. (a) Maximum windowed energy of boluses (crosses) and their constituent candidate swallows (circles and dots denote respectively true and false positive swallows). $\delta_{7,i}$ denotes the maximum energy difference between the $7^{th}$ bolus and its $i^{th}$ candidate swallow. (b) TP and FP changes after applying energy-based FP reduction. The vertical line corresponds to the energy ratios highlighted in Table 1.

Fig. 8. Example of (a) a raw AP bolus signal, (b) segmentation with a FP case (first rectangle), and (c) segmentation after FP removal. The vertical lines indicate the VFSS-identified swallow onsets and the rectangles identify the segmented swallows.

SIGNAL TRIMMING AND FALSE POSITIVE REDUCTION OF POST-SEGMENTATION SWALLOWING ACCELEROMETRY DATA

CROSS REFERENCE TO RELATED APPLICATIONS

The present application is a National Stage of International Application No. PCT/IB2017/000183, filed on Feb. 9, 2017, which claims priority to U.S. Provisional Patent Application No. 62/292,995, filed on Feb. 9, 2016, the entire contents of which are being incorporated herein by reference.

BACKGROUND

The present disclosure generally relates to methods and devices for quantifying swallowing function. More specifically, the present disclosure relates to methods in which adaptive trimming and/or false positive reduction improve the accuracy of automatically segmented swallowing accelerometry data.

Any difficulty in the process of transferring food or liquid from the mouth to the stomach is referred to as dysphagia or swallowing disorder. Dysphagia negatively affects the quality of life of patients through an increased risk of aspiration (the entry of material into the airway below the true vocal folds). Causes of dysphagia include: changes in the anatomical structures necessary for swallowing, as a consequence of surgery, cancer, trauma, or inflammation; genetic malformations of the swallowing apparatus; and neurological impairments due to stroke, Parkinson's disease, cerebral palsy, and acquired brain injury.

The videofluoroscopic swallowing study (VFSS) is the gold standard for the diagnosis of dysphagia. During this procedure, patients swallow different consistencies of barium-coated liquid and food and are exposed to ionizing radiation. In addition, expensive equipment and specialized clinicians are required for VFSS and are not available in every medical establishment. As a result, VFSS cannot be performed on a day-to-day basis.

As a non-invasive adjunct to VFSS, swallowing accelerometry has been introduced, deploying a dual-axis accelerometer on the surface of the patient's neck slightly below the laryngeal prominence (commonly known as Adam's apple) to measure epidermal vibrations accompanying swallowing, in two anatomical directions: anterior-posterior (A-P) and superior-inferior (S-I). A dual-axis accelerometer provides more information relating to swallowing than either axis alone. Quantitative evaluations of the recorded signals obtained from the accelerometer are possible through digital signal processing. Significant correlation between the peak laryngeal movement and the A-P acceleration signal have been reported, while hyolaryngeal excursion has been implicated as the primary physiological source of the two-dimensional signal via semi-partial correlations.

The accelerometry data can be manually segmented into distinct swallowing events that can be individually classified. Manual segmentation may be applied to accelerometry data, for example, upon visual inspection of the data (e.g. identification of the start of each swallowing event, which may be readily and systematically recognized by an operator of the device). However, automatic segmentation using algorithms facilitates segmentation of larger collections of data. Larger volumes of accelerometry data necessitate an automatic method to mitigate human error due to fatigue or oversight and to ensure consistent segmentation criteria.

SUMMARY

The present inventors discovered that automatic segmentation of acceleration signals in anterior-posterior and superior-inferior anatomical directions may be too liberal, admitting pre- and post-swallowing activity while also giving rise to false positive, non-swallow segments. These segmentation shortcomings adversely affect feature extraction and ultimately classification of swallowing function. As set forth in the experimental example disclosed herein, the present inventors found that adaptively trimming the swallow segments (e.g., using a kernel density estimation-based algorithm) and/or performing false positive reduction (e.g., energy-based and/or noise-floor) significantly mitigates these segmentation shortcomings.

Accordingly, in a general embodiment, the present disclosure provides a method of method of swallowing impairment detection, the method comprising subjecting swallowing segments and non-swallowing segments of vibrational data to processing by a processing module. The processing is selected from the group consisting of adaptive trimming, false positive reduction, and a combination thereof. The vibrational data (i) represents swallowing activity, (ii) is from a sensor positioned externally on the throat of a patient and operatively connected to the processing module, and (iii) is associated with at least one axis selected from the group consisting of an anterior-posterior axis and a superior-inferior axis.

In an embodiment, the processing comprises adaptive trimming for each of the at least one axis, the adaptive trimming comprising forming trimmed segments from the swallowing and the non-swallowing segments, each of the trimmed segments comprise a portion of the respective segment corresponding to physiological vibrations associated with swallowing and exclude a portion of the respective segment corresponding to pre-swallow and post-swallow signal fluctuations.

The adaptive trimming can comprise, for each of the at least one axis: using kernel density estimation to obtain probability distributions for the swallowing segments and the non-swallowing segments; determining an energy threshold based at least partially on the probability distributions; and the excluded portion is identified based on an energy difference of the excluded portion falling below the energy threshold. The method can comprise setting a probability cut-off for the probability distributions to adjust an extent of the adaptive trimming.

In an embodiment, the processing comprises false positive reduction selected from the group consisting of energy-based false positive reduction, noise floor-based false positive reduction, and a combination thereof. The energy-based false positive reduction can comprise determining, for each of the least one axis, an axial energy-based bolus-specific threshold and discarding the swallowing segments having a maximum energy value less than the respective bolus-specific threshold. The noise floor-based false positive reduction can comprise generating an amplitude histogram of the vibrational data, using the amplitude histogram to determine an axial threshold for each of the at least one axis, and discarding the swallowing segments having a noise range greater than the respective axial threshold. The method can comprise adjusting an axial threshold to control a balance between removal of false positives and loss of true positives.

In an embodiment, the processing module receives the vibrational data from the sensor and automatically forms the swallowing segments and the non-swallowing segments from the vibrational data.

In an embodiment, the sensor is selected from the group consisting of a single-axis accelerometer and a dual-axis accelerometer.

In an embodiment, the method comprises classifying the swallowing segments and the non-swallowing segments as normal swallowing or a possible swallowing impairment after the processing of the swallowing and non-swallowing segments, and the processing module performs the classifying. The method can comprise generating an output representing the classification, the processing module generates the output. The possible swallowing impairment can comprise at least one of a swallowing safety impairment or a swallowing efficiency impairment. The possible swallowing impairment can comprise penetration or aspiration, and the processing module can further classify the swallowing event as indicative of one of a safe event and an unsafe event.

In another embodiment, the present disclosure provides an apparatus for quantifying swallowing function. The apparatus comprises: a sensor configured to be positioned on the throat of a patient and acquire vibrational data representing swallowing activity and associated with at least one axis selected from the group consisting of an anterior-posterior axis and a superior-inferior axis; and a processing module operatively connected to the sensor and configured to subject swallowing segments and non-swallowing segments of the vibrational data to processing selected from the group consisting of adaptive trimming, false positive reduction, and a combination thereof.

In an embodiment, the apparatus comprises an output component selected from a display, a speaker, and a combination thereof, the processing module configured to classify the swallowing segments and the non-swallowing segments as normal swallowing or a possible swallowing impairment after the processing of the swallowing segments and the non-swallowing segments, the processing module configured to use the output component to indicate the classification visually and/or audibly.

In an embodiment, the processing module is operatively connected to the sensor by at least one of a wired connection or a wireless connection.

In an embodiment, the processing module is configured to receive the vibrational data from the sensor and automatically form the swallowing segments and the non-swallowing segments from the vibrational data.

In another embodiment, the present disclosure provides a method of treating dysphagia in a patient, the method comprising: positioning a sensor externally on the throat of the patient, the sensor acquiring vibrational data representing swallowing activity and associated with at least one axis selected from the group consisting of an anterior-posterior axis and a superior-inferior axis, the sensor operatively connected to a processing module subjecting swallowing segments and non-swallowing segments of the vibrational data to processing selected from the group consisting of adaptive trimming, false positive reduction, and a combination thereof, the processing module generating an output indicative of a classification of the vibrational data; and adjusting a feeding administered to the patient based on the classification.

In an embodiment, the adjusting of the feeding is selected from the group consisting of changing a consistency of the feeding, changing a type of food in the feeding, changing a size of a portion of the feeding administered to the patient, changing a frequency at which portions of the feeding are administered to the patient, and combinations thereof.

An advantage of one or more embodiments provided by the present disclosure is to overcome drawbacks of known techniques for swallowing impairment detection.

Another advantage of one or more embodiments provided by the present disclosure is to reduce inclusion of pre- and post-swallowing activity in automatically segmented swallowing accelerometry data.

A further advantage of one or more embodiments provided by the present disclosure is to reduce false positive, non-swallow segments in automatically segmented swallowing accelerometry data.

Yet another advantage of one or more embodiments provided by the present disclosure is to improve feature extraction in automatically segmented swallowing accelerometry data.

Another advantage of one or more embodiments provided by the present disclosure is to improve classification of swallowing function based on automatically segmented swallowing accelerometry data.

A further advantage of one or more embodiments provided by the present disclosure is to minimize loss of true positives (e.g., at most a moderate loss) while significantly reducing the number of false positive swallow segments in classification of swallowing function based on automatically segmented swallowing accelerometry data.

Yet another advantage of one or more embodiments provided by the present disclosure is to enable a user to control algorithmic thresholds to adjust the balance between false positive reduction and loss of true positives in classification of swallowing function based on automatically segmented swallowing accelerometry data.

Another advantage of one or more embodiments provided by the present disclosure is to classify swallows in greater detail than is possible in known methods.

A further advantage of one or more embodiments provided by the present disclosure is to extract individual swallows with a higher accuracy rate than is possible in known methods.

Additional features and advantages are described herein, and will be apparent from, the following Detailed Description and the Figures.

DETAILED DESCRIPTION

As used in this disclosure and the appended claims, the singular forms "a," "an" and "the" include plural referents unless the context clearly dictates otherwise. As used herein, "about" is understood to refer to numbers in a range of numerals, for example the range of −10% to +10% of the referenced number, preferably -5% to +5% of the referenced number, more preferably -1% to +1% of the referenced number, most preferably -0.1% to +0.1% of the referenced number. Moreover, all numerical ranges herein should be understood to include all integers, whole or fractions, within the range.

The words "comprise," "comprises" and "comprising" are to be interpreted inclusively rather than exclusively. Likewise, the terms "include," "including" and "or" should all be construed to be inclusive, unless such a construction is clearly prohibited from the context. A disclosure of a device "comprising" several components does not require that the components are physically attached to each other in all embodiments.

Nevertheless, the devices disclosed herein may lack any element that is not specifically disclosed. Thus, a disclosure of an embodiment using the term "comprising" includes a disclosure of embodiments "consisting essentially of and "consisting of" the components identified. Similarly, the methods disclosed herein may lack any step that is not specifically disclosed herein. Thus, a disclosure of an embodiment using the term "comprising" includes a disclosure of embodiments "consisting essentially of and "consisting of the steps identified.

The term "and/or" used in the context of "X and/or Y" should be interpreted as "X," or "Y," or "X and Y." Where used herein, the terms "example" and "such as," particularly when followed by a listing of terms, are merely exemplary and illustrative and should not be deemed to be exclusive or comprehensive. Any embodiment disclosed herein can be combined with any other embodiment disclosed herein unless explicitly stated otherwise.

An aspect of the present disclosure is a method of processing segmented dual-axis accelerometry signals for the indication of problematic swallowing events, such as dysphagia or aspiration. Non-limiting examples of such methods include a method of quantifying swallowing function and a method of swallowing impairment detection. Another aspect of the present disclosure is a device that implements one or more steps of the method.

In some embodiments, the method and the device can be employed in the apparatus and/or the method for detecting aspiration disclosed in U.S. Pat. No. 7,749,177 to Chau et al., the method and/or the system of segmentation and time duration analysis of dual-axis swallowing accelerometry signals disclosed in U.S. Patent App. Publ. No. 8,267,875 to Chau et al., the system and/or the method for detecting swallowing activity disclosed in U.S. Pat. No. 9,138,171 to Chau et al., or the method and/or the device for swallowing impairment detection disclosed in U.S. Patent App. Publ. No. 2014/0228714 to Chau et al., each of which is incorporated herein by reference in its entirety.

As used herein, "aspiration" is entry of food or drink into the trachea (windpipe) and lungs and can occur during swallowing and/or after swallowing (post-deglutitive aspiration). Post-deglutitive aspiration generally occurs as a result of pharyngeal residue that remains in the pharynx after swallowing.

Figure 1:
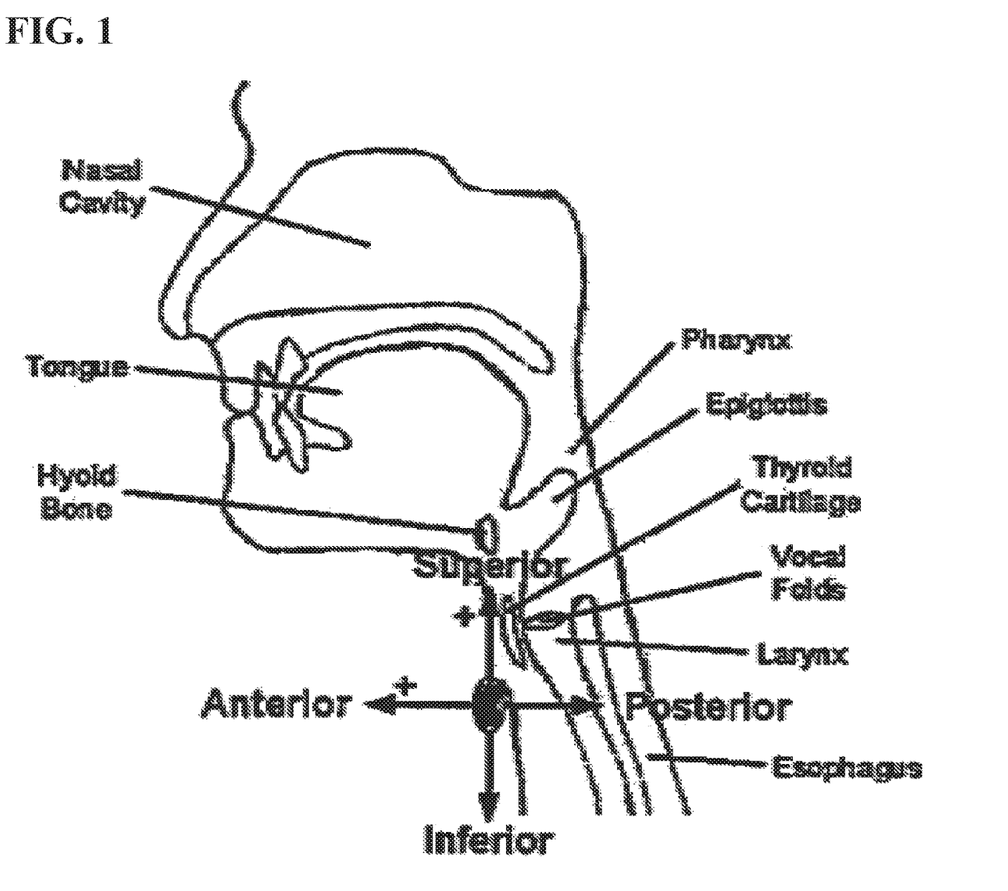
FIG. 1 is diagram showing the axes of acceleration in the anterior-posterior and superior-inferior directions.

As discussed in greater detail hereafter, the device may include a sensor configured to produce signals indicating swallowing activities (e.g., a single axis accelerometer or a dual axis accelerometer). The sensor may be positioned externally on the neck of a human, preferably anterior to the cricoid cartilage of the neck. A variety of means may be applied to position the sensor and to hold the sensor in such position, for example double-sided tape. Preferably the positioning of the sensor is such that the axes of acceleration are aligned to the anterior-posterior and super-inferior directions 10, as shown in FIG. 1.

Figure 2:
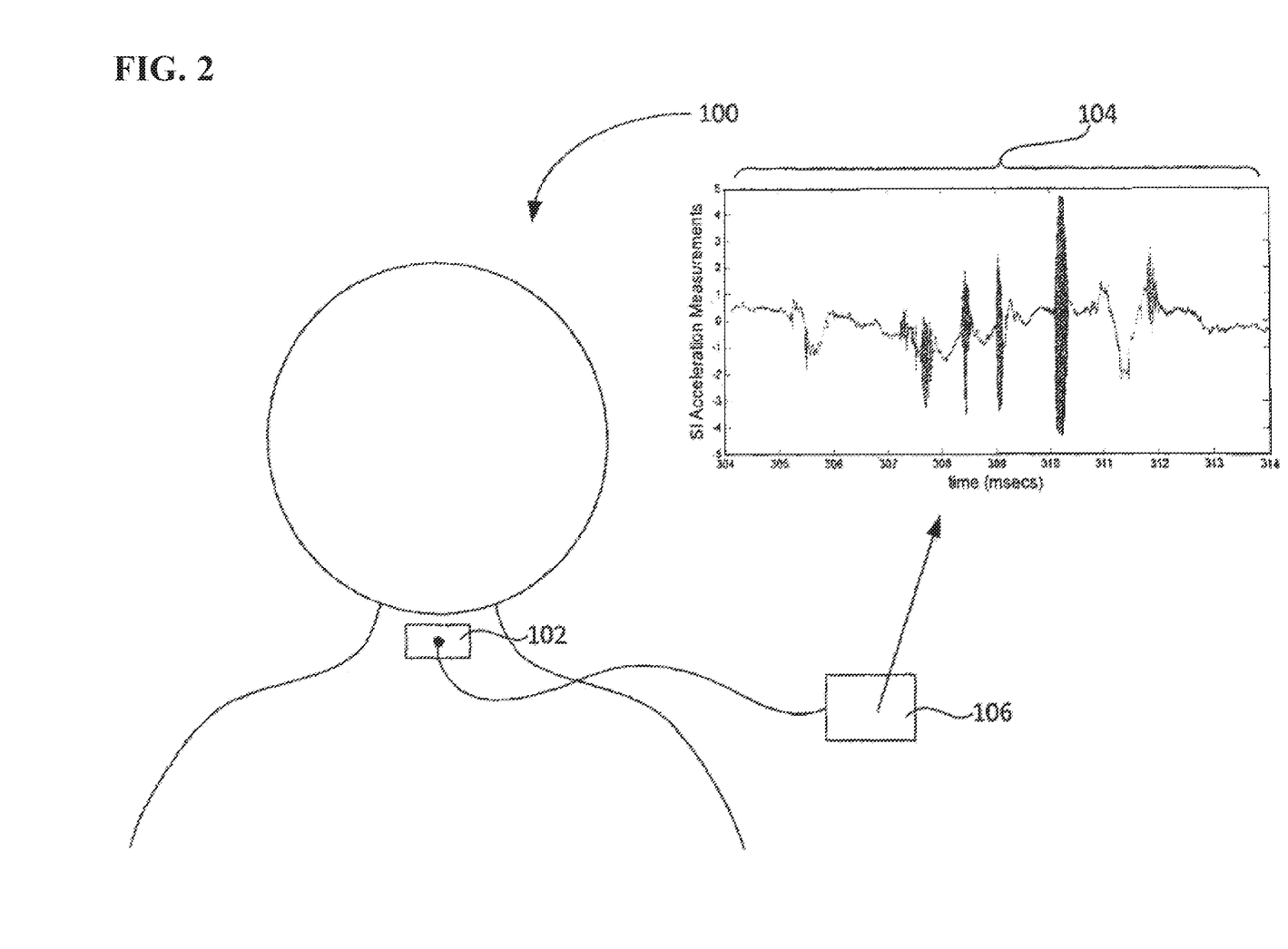
FIG. 2 is a schematic diagram of an embodiment of a swallowing impairment detection device in operation.

FIG. 2 generally illustrates a non-limiting example of a device 100 for use in swallowing impairment detection. The device 100 can comprise a sensor 102 (e.g., a single axis accelerometer or a dual axis accelerometer) to be attached in a throat area of a candidate for acquiring dual axis accelerometry data and/or signals during swallowing, for example illustrative S-I acceleration signal 104. Accelerometry data may include, but is not limited to, throat vibration signals acquired along the anterior-posterior axis (A-P) and/or the superior-inferior axis (S-I). The sensor 102 can be any accelerometer known to one of skill in this art, for example an EMT 25-C single axis accelerometer or an ADXL322 dual axis accelerometer, and the present disclosure is not limited to a specific embodiment of the sensor 102.

The sensor 102 can be operatively coupled to a processing module 106 configured to process the acquired data for swallowing impairment detection, for example aspiration detection and/or detection of other swallowing impairments such as swallowing inefficiencies. The processing module 106 can be a distinctly implemented device operatively coupled to the sensor 102 for communication of data thereto, for example, by one or more data communication media such as wires, cables, optical fibres, and the like and/or by one or more wireless data transfer protocols. In some embodiments, the processing module 106 may be implemented integrally with the sensor 102.

The signal acquisition by the sensor 102 and the processing of the signal by the processing module 106, which are described in greater detail hereafter, are generally discussed in the context of the preferred embodiment in which a dual axis accelerometer is used to obtain both A-P and S-I vibrational data. However, the present disclosure also encompasses embodiments in which a single axis accelerometer is used. In this regard, the disclosures regarding the data from the corresponding single axis (A-P or S-I) which are provided in the context of a dual axis accelerometer can also be applied to embodiments in which a single axis accelerometer is used. For example, processing of A-P data in the context of a dual axis accelerometer can be applied similarly to A-P data obtained by a single axis accelerometer (e.g., in the absence of S-I data), and processing of S-I data in the context of a dual axis accelerometer can be applied similarly to S-I data obtained by a single axis accelerometer (e.g., in the absence of A-P data). Further in this regard, the reduced inclusion of pre- and post-swallowing activity in automatically segmented swallowing accelerometry data can be achieved by both single axis and dual axis embodiments.

Figure 3:
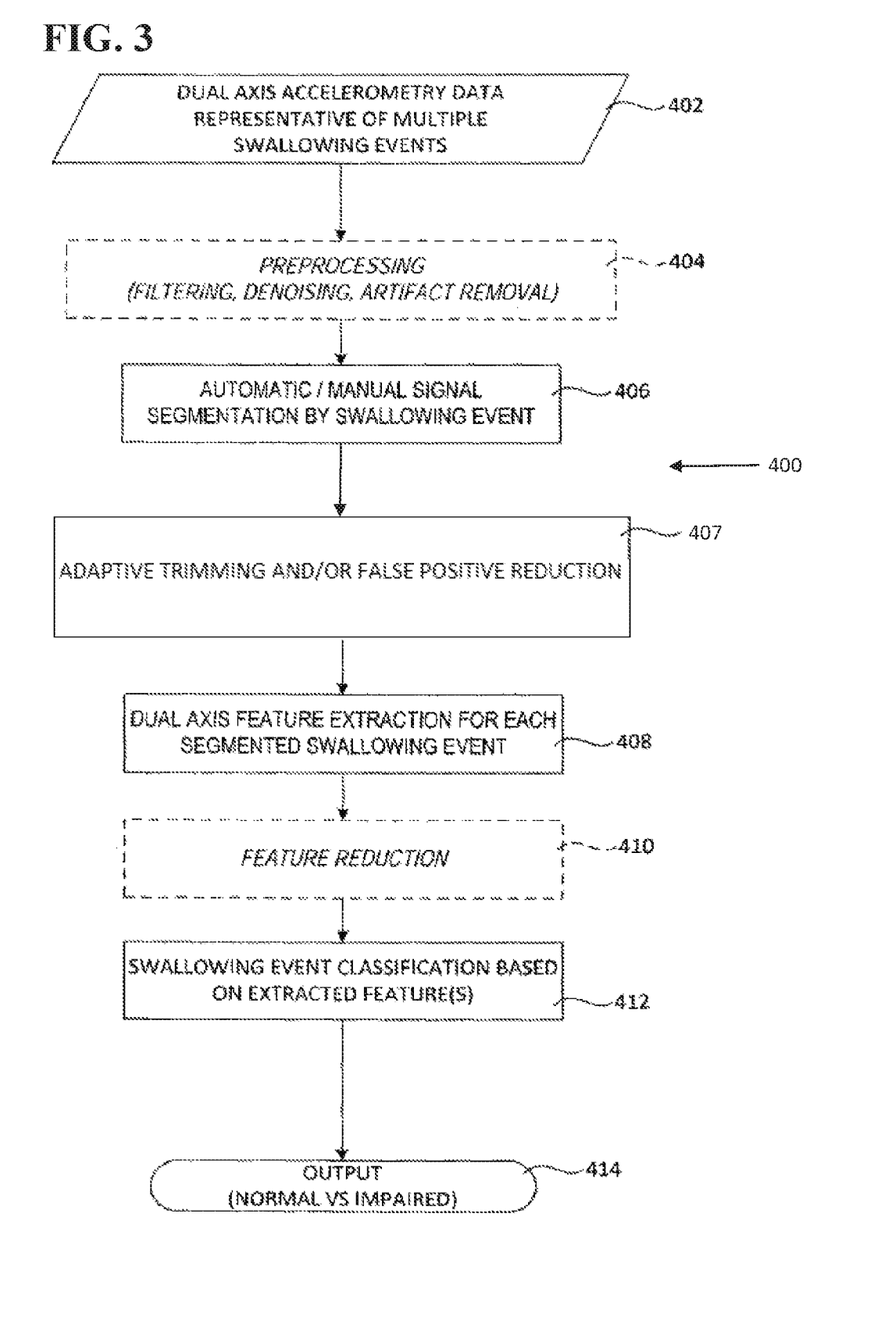
FIG. 3 is a flowchart of a dual axis accelerometry data processing method for implementation by a swallowing impairment detection device.

FIG. 3 generally illustrates a non-limiting example of a method 400 of swallowing impairment detection, wherein optional steps in this embodiment are shown in dashed-line boxes. At Step 402, accelerometry data ("raw data") can be acquired from multiple swallowing events, for example by an accelerometer such as sensor 102. At Step 404, the accelerometry data can optionally be processed to condition the accelerometry data and thus facilitate further processing thereof. For example, the accelerometry data may be filtered, denoised and/or processed for signal artifact removal ("pre-processed data").

At Step 406, the accelerometry data (either raw or pre-processed) can then be automatically or manually segmented into distinct swallowing events. Preferably the accelerometry data is automatically segmented. In an embodiment, the accelerometry data is automatically segmented as disclosed in U.S. Pat. No. 8,267,875 to Chau et al., the entirety of which is incorporated herein by reference as noted above. For example, the automatic segmentation can comprise applying fuzzy c-means optimization to the data determine the time boundaries for each of the swallowing and non-swallowing segments. Additionally or alternatively, manual segmentation may be applied, for example by visual inspection of the data. The method 400 is not limited to a specific embodiment of the segmented data.

At Step 407, the segmented accelerometry data can be subjected to adaptive signal trimming and/or false positive reduction. The resultant event-specific data can then be processed for dual axis feature extraction at Step 408, and optionally processed for feature reduction at Step 410. In embodiments where the data is single-axis data, the extracted features preferably comprise one or more of stationarity, normality and dispersion ratio. In embodiments where the data is dual-axis data, the extracted features preferably comprise a log energy of vibrational data acquired along the A-P axis and an entropy of vibrational data acquired along the S-I axis, for example a log energy of each level of an 18 level sym8 wavelet decomposition of the vibrational data acquired along the A-P axis and an entropy of each level of a 12 level sym8 wavelet decomposition of said vibrational data acquired along the S-I axis. The present disclosure is not limited to a specific embodiment of the extracted features.

Each swallowing event can then be classified based on the extracted features at Step 412. In an embodiment where the data is single-axis data, the classification is preferably performed using a radial basis function neural network implemented by the processing module 106 to classify swallowing events in real-time, as either swallows or aspirations. In an embodiment where the data is dual-axis data, the classification is preferably performed by comparing the extracted features with preset classification criteria defined by features previously extracted and classified from a known training data set, for example as a function of a distance of the extracted features from the classification criteria (e.g., discriminant analysis using Mahalanobis distances with stratified covariance estimates). The present disclosure is not limited to a specific embodiment of the classifying process.

The classification can be used to determine and output which swallowing event represented a normal swallowing event as compared to a penetration, an aspiration, a swallowing safety impairment and/or an swallowing efficiency impairment at Step 414. In some embodiments, the swallowing event can be further classified as a safe event or an unsafe event.

For example, the processing module 106 and/or a device associated with the 106 can comprise a display that identifies a swallow or an aspiration using images such as text, icons, colors, lights turned on and off, and the like. Alternatively or additionally, the processing module 106 and/or a device associated with the processing module 106 can comprise a speaker that identifies a swallow or an aspiration using auditory signals. The present disclosure is not limited to a specific embodiment of the output, and the output can be any means by which the classification of the swallowing event is identified to a user of the device 100, such as a clinician or a patient.

The output may then be utilized in screening/diagnosing the tested candidate and providing appropriate treatment, further testing, and/or proposed dietary or other related restrictions thereto until further assessment and/or treatment may be applied. For example, adjustments to feedings can be based on changing consistency or type of food and/or the size and/or frequency of mouthfuls being offered to the patient.

Alternative types of vibration sensors other than accelerometers can be used with appropriate modifications to be the sensor 102. For example, a sensor can measure displacement (e.g, a microphone), while the processing module 106 records displacement signals over time. As another example, a sensor can measure velocity, while the processing module 106 records velocity signals over time. Such signals can then be converted into acceleration signals and processed as disclosed herein and/or by other techniques of feature extraction and classification appropriate for the type of received signal.

As noted above, Step 407 comprises subjecting the segmented accelerometry data to adaptive signal trimming and/or false positive reduction, and preferred embodiments of these processes are disclosed below.

Adaptive Signal Trimming

Adaptive signal trimming can trim the segmented accelerometry data so that the resultant data comprises the portion of the signal corresponding to the physiological vibrations associated with swallowing, while excluding the pre- and post-swallow signal fluctuations. Preferably the trimmed data consists of the portion of the signal corresponding to the physiological vibrations associated with swallowing.

The adaptive signal trimming can comprise determining the base energy ($E_{base}$) within a window of a predetermined number of samples w (e.g., w=500) that are centered at the location of the peak amplitude value of the segmented swallow (S):

$$E_{base}^{AP} = \sum_{i=p-\frac{w}{2}}^{p+\frac{w}{2}} (i^{AP})^2 \quad \text{(Equation 1)}$$

where $i^{AP}$ is the A-P signal, p is the peak index, and w is the window size.

$L_S$ can be the length of the initially segmented swallow, and a corresponding non-swallow segment NS can be defined as the segment of length $L_S$ with the minimum signal energy within a predetermined time period of the beginning of the signal (e.g., the first 10 seconds of the calibration signal, given that typical swallows are approximately 1 second in duration).

Then the adaptive trimming can comprise moving the window w by a predetermined sample increment s (e.g., s=50 samples) along the swallow and non-swallow segments (e.g., with 90% overlap). Then the adaptive trimming can comprise determining the energy differences between the base energy $E_{base}$ and the energy within the moving windows. For the A-P signal, these differences are preferably determined as:

$$\Delta E_S^{AP}(j) = |E_{base}^{AP} - E_S^{AP}(j)|, 1 \le j \le \left\lfloor \frac{L_s - w + s}{s} \right\rfloor \quad \text{(Equation 2)}$$

$$\Delta E_{NS}^{AP}(j) = |E_{base}^{AP} - E_{NS}^{AP}(j)| \quad \text{(Equation 3)}$$

where $E_S^{AP}$ and $E_{NS}^{AP}$ are the energy differences of the swallow and non-swallow segments, respectively, and $$E_S^{AP}(j) = \sum_{i=1+(j-1)s}^{w+(j-1)s} (i^{AP})^2, 1 \le j \le \left\lfloor \frac{L_s - w + s}{s} \right\rfloor \quad \text{(Equation 4)}$$

Preferably, $E_{NS}^{AP}(j)$ is similarly defined using the non-swallow segment NS.

The adaptive trimming can further comprise applying the above formulation to the S-I signal. Nevertheless, in some embodiments (e.g., those using a single axis accelerometer), the above formulation is applied to only one of the A-P axis or the S-I axis.

The adaptive trimming can further comprise determining the probability density of energy differences for both swallow and non-swallow segments from their respective histograms using kernel density estimation, for example as disclosed by M. Di Marzio and C. C. Taylor in "Kernel density classification and boosting: an L2 analysis," Statistics and Computing 15(2):113-123 (April 2005). Additionally or alternatively, other methods of determining the probability density of the energy differences can be used.

In embodiments using kernel density classification, x, denotes the histogram bin counts of energy difference values i=1, . . . , N. The estimated kernel density of energy differences d(x) is:

$$\hat{d}(x) = \frac{1}{Nh} \sum_{i=1}^{N} K\left(\frac{x - x_i}{h}\right) \quad \text{(Equation 5)}$$

where K is the kernel function, N is the number of energy difference distribution bins, and h is the kernel smoothing bandwidth. Given the versatile estimation capabilities of a Gaussian mixture, a Gaussian kernel can be adopted:

$$K\left(\frac{x - x_i}{h}\right) = \frac{1}{\sqrt{2\pi}} e^{-\frac{(x-x_i)^2}{2h^2}} \quad \text{(Equation 6)}$$

The adaptive trimming can comprise estimating the bandwidth of the kernel:

$$h = 1.066\sigma N^{A;5} \quad \text{(Equation 7)}$$

where $\sigma$ is the standard deviation of the energy differences.

$C(x) \in \{swallow, non\text{-}swallow\}$ can represent the predicted label for an energy difference x. The adaptive trimming can comprise determining the probability of an energy difference x belonging to the swallow class:

$$P(C(x) = \text{swallow} | X = x) = \frac{p_S \hat{d}_S(x)}{p_S \hat{d}_S(x) + p_{NS} \hat{d}_{NS}(x)} \quad \text{(Equation 8)}$$

where $\hat{d}_S(x)$ and $\hat{d}_{NS}(x)$ are the estimated densities for swallow and non-swallow segments, while $p_S = p_{NS} = 0.5$ are the swallow and non-swallow priors, respectively.

The adaptive trimming can comprise applying the above formulation to both A-P and S-I signals. Again, in some embodiments (e.g., those using a single axis accelerometer), the above formulation is applied to only one of the A-P axis or the S-I axis.

The adaptive trimming can comprise obtaining probability distributions for swallow and non-swallow segments. Setting a probability cut-off can obtain energy thresholds $T^{AP}$ and $T^{SI}$ for each channel. The higher the probability cut-off, the more aggressive the trimming. Preferably, trimming the swallow segments comprises identifying the location of the peak amplitude, then shifting overlapping windows of size w to the left and to the right of the peak by increments of size s, and calculating the energy difference within each window w. Bilaterally, windowed segments with energy difference below the threshold can be removed from the candidate swallow segment.

False Positive Reduction

Figure 4:
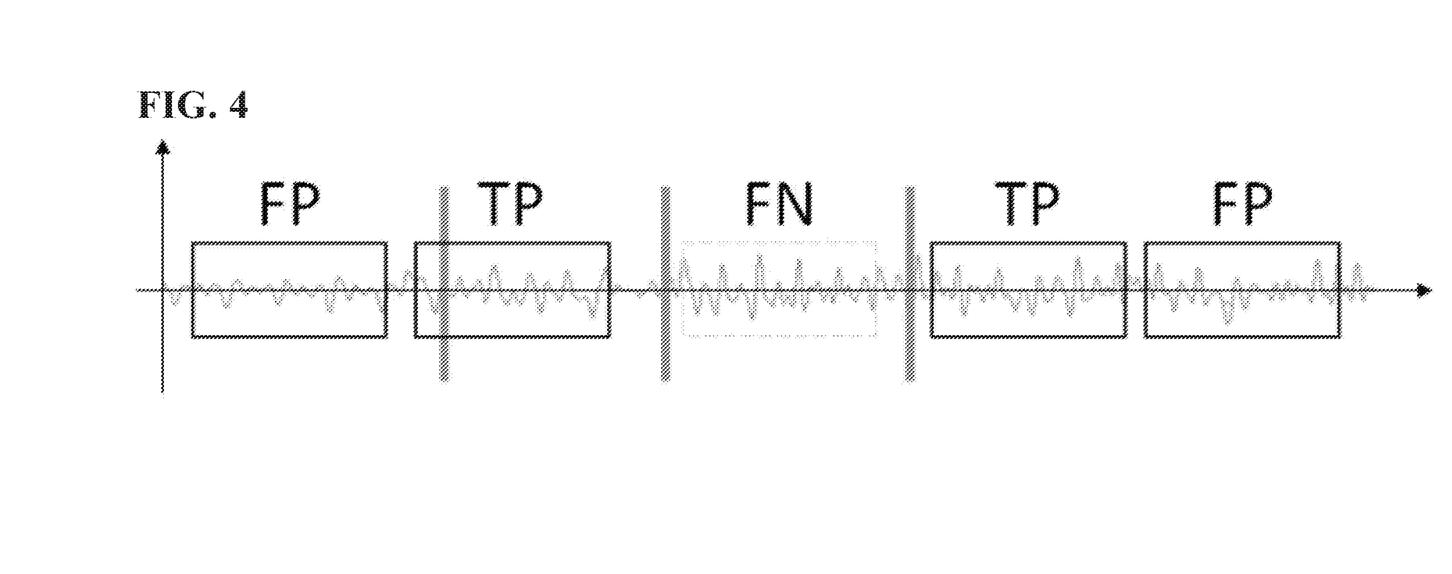
FIG. 4 is a schematic diagram of an accelerometry signal in which False Positive (FP), True Positive (TP) and False Negative (FN) segments are defined.

The relevant performance metrics for false positive reduction are discussed hereafter. FIG. 4 defines False Positive (FP), True Positive (TP) and False Negative (FN) segments. In this figure, vertical lines correspond to VFSS-demarcated swallow onsets, and rectangles denote candidate swallow segments. True Positive (TP) refers to an automatically segmented swallow candidate where a videofluoroscopy-demarcated swallow onset precedes or falls within the candidate segment boundaries. False Positive (FP) refers to an automatically segmented swallow candidate that does not have a videofluoroscopy-demarcated swallow onset neither within nor preceding the candidate segment boundaries. False Negative (FN) occurs when no swallows are segmented for a particular videofluoroscopic swallow onset.

"TP change" refers to the percent change in the number of TP cases, i.e., TP change=$(TP_{new} - TP_{existing})/(TP_{existing})$. "FP change" refers to the percent change in the number of FP segments. Recall (R), also known as sensitivity, measures the proportion of swallow segments that are correctly identified, i.e., R=TP/(TP+FN). Precision (P) is a measure of fidelity and equals one minus the FP rate, i.e., P=TP/(TP+FP). Precision (P) is also known as the positive predictive value. Harmonic average (F) is a combined measure of recall and precision, i.e., F=(2 R P)/(P+R).

The false positive reduction preferably comprises energy-based false positive reduction and/or noise floor-based false positive reduction, each of which is explained in turn hereafter.

Energy-Based False Positive Reduction

Energy-based false positive reduction is based on adaptive energy-based thresholding. The energy-based false positive reduction can comprise deriving, for each axis, a bolus-specific threshold $T_b$ based on the axial energy of the bolus:

$$T_b^{AP} = \Lambda^{AP} \times \hat{E}_b^{AP}$$

where $\hat{E}_b^{AP}$ is the maximum energy calculated within a moving window of a predetermined number of samples (e.g., 500 samples) on the A-P channel for a specific bolus b, and $\Lambda^{AP}$ is a data-dependent scalar.

The energy-based false positive reduction can comprise determining $T_b^{SI}$ for the S-I channel, using the same procedure. For each candidate swallow, the energy can be estimated within overlapping windows (e.g., 50% overlapping), each of predetermined number of samples (e.g., 500 samples each). The energy-based false positive reduction can comprise discarding the candidate swallow if the maximum energy value across these windows was less than the corresponding bolus-adaptive threshold (either $T_b^{AP}$ and $T_b^{SI}$). The scalars $\Lambda^{AP}$ and $\Lambda^{SI}$ can be estimated by the following approaches, namely energy ratio and maximum energy difference.

For the energy ratio approach to scalar estimation, segmental scalars for each channel ($\lambda_{b,i}^{AP}$ and $\lambda_{b,i}^{SI}$) can be determined for each swallow segment as:

$$\lambda_{b,i}^{AP} = \frac{\hat{E}_{b,i}^{AP}}{\hat{E}_b^{AP}}, \text{ and } \lambda_{b,i}^{SI} = \frac{\hat{E}_{b,i}^{SI}}{\hat{E}_b^{SI}} \qquad \text{(Equation 9)}$$

where $i \geq 1$ indexes the number of the detected swallow segment within bolus b, and $\hat{E}_{b,i}^{AP}$ and $\hat{E}_{b,i}^{SI}$ are the maximum axial energies of the $i^{th}$ swallow segment of bolus b.

The denominators are the maximum energies over the entire bolus. As above, all energies are preferably estimated within a moving window of predetermined number of samples (e.g., 500 samples) with a predetermined overlap (e.g., 50%). The scalars for the A-P and S-I channels ($\Lambda^{AP}$ and $\Lambda^{SI}$) can then be estimated as a linear combination of the average (mean) and standard deviation (std) of the candidate scalars. For example, in an embodiment, an estimate for the A-P scalar with j=0, 1, 2 can be:

$$\Lambda^{AP} = \text{mean}(\lambda_{b,i}^{AP}) - j \times \text{std}(\lambda_{b,i}^{AP}) \qquad \text{(Equation 10)}$$

The maximum energy difference approach to scalar estimation is based on the recognition that FP segments generally have lower maximum windowed energy than TP segments. An energy difference approach was thus devised in which the maximum energy difference for bolus b can be defined as:

$$\delta_{b,*}^{AP} = \hat{E}_b^{AP} - \hat{E}_{b,*}^{AP} \qquad \text{(Equation 11)}$$

where $\hat{E}_b^{AP}$ is the maximum windowed energy of bolus b, and $\hat{E}_{b,*}^{AP} = \min_i \hat{E}_{b,i}^{AP}$. $\Delta^{AP}$ can be defined as the set of $\delta_{b,*}^{AP}$ that satisfy the following:

$$\Delta^{AP} = \{\delta_{b,*}^{AP} | \forall b: \delta_{b,*}^{AP} \geq \max_b(\delta_{b,*}^{AP}) \times \beta\} \qquad \text{(Equation 12)}$$

where $\beta \in (0,1]$ is an empirically tuned scalar to suit the characteristics of the signals of interest. In this set, there exists swallow segment i' within bolus b', for which the energy ratio, $\lambda_{b,i}^{AP}$, defined in Equation 9 is maximized:

$$\{\exists! \; b', i' | \lambda_{b',i'}^{AP} \geq \lambda_{b,i}^{AP}; \forall b: \delta_{b,*}^{AP} \in \Delta^{AP}, i \in I_b, i' \in I_{b'}\} \qquad \text{(Equation 13)}$$

where $I_b$ and $I'_b$ are the sets of candidate swallow indices for boluses b and b', respectively. Finally, the scalar $\Lambda^{AP}$ is set as the energy ratio of swallow segment i' within bolus b': $\Lambda^{AP} = \lambda_{b',i'}^{AP}$.

$\Lambda^{SI}$ can be estimated by following the same procedure for the S-I axis.

Noise-Floor False Positive Reduction

Noise-floor false positive reduction comprises only accepting candidates whose range exceeds that of the noise floor. In embodiments where both energy-based false positive reduction and noise-floor false positive reduction are used, the noise-floor false positive reduction can further reduce false positives. Most of the noise is typically low energy, so the noise-floor algorithm can comprise determining the amplitude histogram of the bolus signal. Therefore, the noise-floor false positive reduction can comprise estimating the range of the noise signal as $\alpha \times \sigma$, where $\sigma$ is initially the bolus variance and $\alpha$ is a scalar multiplier (i.e., assuming that the noise resided within $\mu + \alpha \sigma 0$ and $\mu - \alpha \sigma$). The axial thresholds are then determined as:

$$T^{AP} = \alpha^{AP} \times \sigma^{AP}, \text{ and } T^{SI} = \alpha^{SI} \times \sigma^{SI} \qquad \text{(Equation 14)}$$

Preferably the noise-floor false positive reduction comprises re-estimating the noise signal range each time a swallow is detected and "removed" from the bolus.

To estimate the optimum values for $\alpha^{AP}$ and $\alpha^{SI}$, the following criterion function can be considered:

$$J(\alpha^{AP}, \alpha^{SI}) = n_{TP}(\alpha^{AP}, \alpha^{SI}) - n_{FP}(\alpha^{AP}, \alpha^{SI}) \qquad \text{(Equation 15)}$$

where TP and FP are the number of $n_{TP}$ and $n_{FP}$ cases, expressed as a function of A-P and S-I scalars ($\alpha^{AP}$, $\alpha^{SI}$) respectively.

The optimal A-P and S-I scalars can be given by:

$$\alpha^{AP*}, \alpha^{SI*} = \underset{\alpha^{AP}, \alpha^{SI}}{\arg\max} J \qquad \text{(Equation 16)}$$

The energy and noise-floor false positive reduction methods are preferably applied in parallel on segmented, preprocessed data. In an embodiment, only candidate segments identified as valid by at least one of the two false positive reduction methods is admitted.

Another aspect of the present disclosure is a method of treating dysphagia. The term "treat" includes both prophylactic or preventive treatment (that prevent and/or slow the development of dysphagia) and curative, therapeutic or disease-modifying treatment, including therapeutic measures that cure, slow down, lessen symptoms of, and/or halt progression of dysphagia; and treatment of patients at risk of dysphagia, for example patients having another disease or medical condition that increase their risk of dysphagia relative to a healthy individual of similar characteristics (age, gender, geographic location, and the like). The term does not necessarily imply that a subject is treated until total recovery. The term "treat" also refers to the maintenance and/or promotion of health in an individual not suffering from dysphagia but who may be susceptible to the development of dysphagia. The term "treat" also includes the potentiation or otherwise enhancement of one or more primary prophylactic or therapeutic measures. The term "treat" further includes the dietary management of dysphagia or the dietary management for prophylaxis or prevention of dysphagia. A treatment can be conducted by a patient, a clinician and/or any other individual or entity.

The method of treating dysphagia comprises using any embodiment of the device 100 disclosed herein and/or performing any embodiment of the method 400 disclosed herein. For example, the method of treating dysphagia can comprise positioning a sensor externally on the throat of the patient, the sensor acquiring vibrational data that represents swallowing activity and associated with at least one axis selected from the group consisting of an anterior-posterior axis and a superior-inferior axis. The sensor is preferably operatively connected to a processing module subjecting swallowing segments and non-swallowing segments of the vibrational data to processing selected from the group consisting of adaptive trimming, false positive reduction, and a combination thereof, and the processing module generates an output indicative of a classification of the vibrational data.

The method can further comprise adjusting a feeding administered to the patient based on the classification, for example by changing a consistency of the feeding, changing a type of food in the feeding, changing a size of a portion of the feeding administered to the patient, changing a frequency at which portions of the feeding are administered to the patient, or combinations thereof.

In an embodiment, the method prevents aspiration pneumonia from dysphagia.

In an embodiment, the dysphagia is oral pharyngeal dysphagia associated with a condition selected from the group consisting of cancer, cancer chemotherapy, cancer radiotherapy, surgery for oral cancer, surgery for throat cancer, a stroke, a brain injury, a progressive neuromuscular disease, neurodegenerative diseases, an elderly age of the patient, and combinations thereof. As used herein, an "elderly" human is a person with a chronological age of 65 years or older.

EXAMPLE

The following experimental example presents scientific data developing and supporting the concept of adaptive trimming and/or false positive reduction improving the accuracy of automatically segmented swallowing accelerometry data.

Dual-axes acceleration signals were acquired using a biaxial accelerometer (ADXL327) with sensitivity of ±2g from 264 consenting adult participants referred to VFSS. The protocol was approved by the research ethics boards of the participating hospitals. The signals were collected via a two-channel custom USB audio interface, consisting of a high-pass filter with 0.1 Hz cut-off to remove the DC or the gravity component from the signals and a low-pass filter with 3 kHz cutoff for each channel. The signals from each axis were sampled at 10 kHz with 12-bit resolution. Data were stored by a custom LabVIEW program running on a laptop for subsequent offline analysis. Participants were asked to perform a calibration task, which included rest, coughing, and counting. Participants were then instructed to take 6 sips of water followed by 6 sips of barium-coated liquids of different consistencies. The acceleration signals were recorded concurrent to the videofluoroscopy recordings. The signals were annotated by speech language pathologists. Over 3,000 usable boluses were identified.

Figure 5:
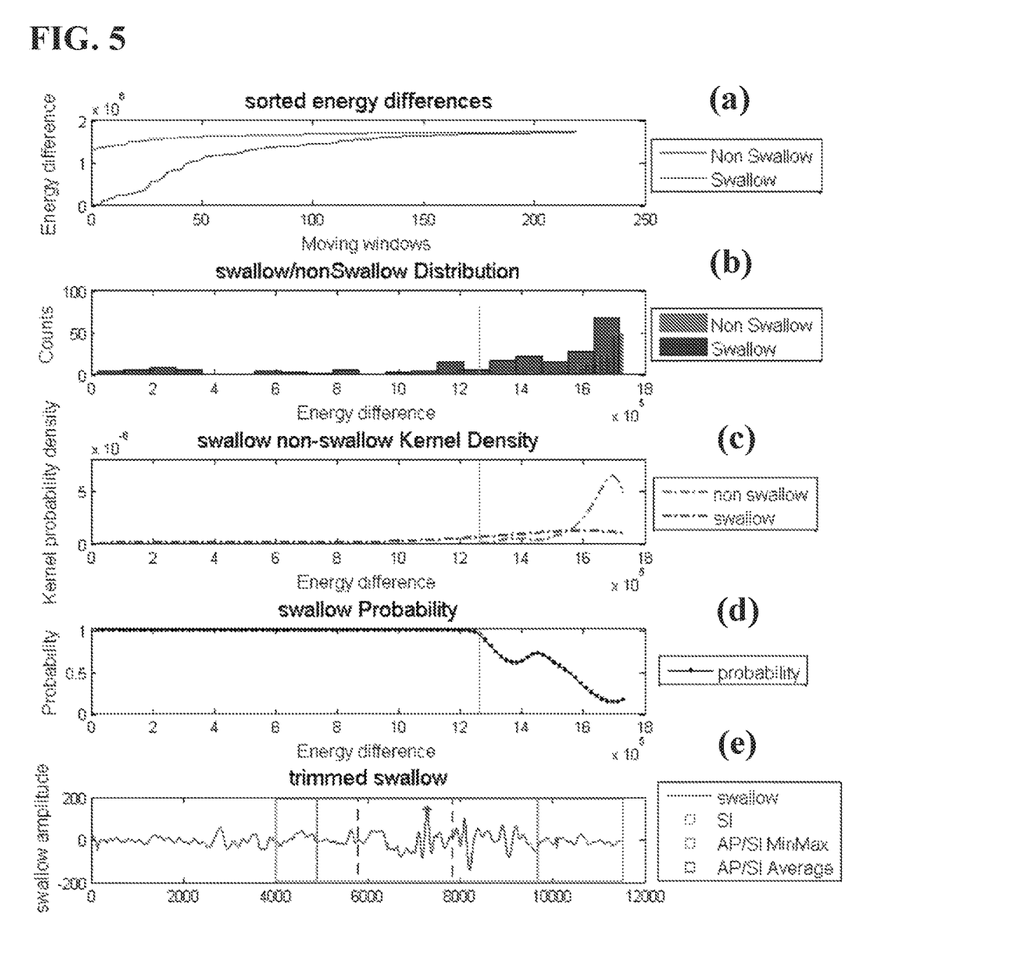
FIGS. 5a-5e are graphs showing swallow trimming based on dual-directional energy differences in the experimental example disclosed herein.

Preprocessing and swallow segmentation were performed as follows. Signals were preprocessed by de-noising, head movement removal, and speech removal. High frequency noise was further suppressed via wavelet packet decomposition with a 4-level discrete Meyer wavelet and shannon entropy A-P and S-I variance signals were computed by estimating the sample variance within windows of size 200 data points, shifted along each of the AP and SI signals with 50% overlap. The swallows were then segmented by subjecting the variance signals to a sequential fuzzy c-means algorithm. However, automatic segmentation by this method, as well as by neural network or quadratic variation, tends to yield segment boundaries that are too lenient, admitting non-swallow activity pre- and post-swallow (FIG. 5e). Likewise, segmentation is prone to identify non-swallow artifacts, resulting in false positives segments (FIG. 8b). To address both of these issues, the present inventors designed the algorithms disclosed above and experimentally utilized as follows.

Adaptive swallow trimming was performed by calculating the base energy Ebase within a window of size w=500 samples centred at the location of the peak amplitude value of the segmented swallow S, according to Equation 1. A corresponding non-swallow segment NS was defined as the segment of length $L_S$ with the minimum signal energy within the first 10 seconds of the calibration signal. Then the window slides by an increment of s=50 samples along the swallow and non-swallow segments with 90% overlap, and the energy differences between the base energy and the energy within the moving windows were calculated according to Equations 2-4. FIG. 5a depicts an example of these energy differences for one swallow. The same formulation was applied to the S-I signal.

The probability density of energy differences for both swallow and non-swallow segments were then estimated from their respective histograms (FIG. 5b) using kernel density estimation, according to Equations 5-7. FIG. 5c shows the probability density estimations of both swallow and non-swallow segments. Again, the above formulation was applied to both AP and SI signals.

Integrating the densities, the probability distributions for swallow and non-swallow segments were obtained. By setting a probability cutoff, the energy thresholds $T^{AP}$ and $T^{SI}$ were determined for each channel. A probability cutoff 0.9 was determined to be suitable for the problem at hand, as exemplified in FIG. 5d, where $T^{SI}=1.26\times10^6$. The vertical green line marks the energy difference where the swallowing class probability exceeds 0.9. This energy threshold is also plotted on FIGS. 5b and 5c.

FIG. 5e illustrates the S-I signal of a swallow segment. The black dashed rectangle marks the trimming boundary achieved considering only the S-I channel. In order to select the same portion of the A-P and S-I signals, the present inventors adopted two approaches. The first approach selected the left- and right-most boundaries of the A-P and S-I segments (marked by the green rectangle). The second approach calculated the midpoint of the two boundaries of A-P and S-I segments (marked by a red rectangle).

Energy-based false positive reduction was performed. For each axis, a bolus-specific threshold $T_b$ was derived based on the axial energy of the bolus:

$$T_b^{AP} = \Lambda^{AP} \times \hat{E}_b^{AP}$$

where $\hat{E}_b^{AP}$ was the maximum energy calculated within a moving window of size 500 samples on the A-P channel for a specific bolus b, and $\Lambda^{AP}$ was a data-dependent scalar.

$T_b^{SI}$ was be determined using the same procedure, but for the S-I channel. For each candidate swallow, the energy was estimated within 50% overlapping windows of 500 samples. The candidate swallow was discarded if the maximum energy value across these windows was less than the corresponding bolus-adaptive threshold (either $T_b^{AP}$ and $T_b^{SI}$). The scalars $\Lambda^{AP}$ and $\Lambda^{SI}$ were estimated by energy ratio and maximum energy difference approaches.

For the energy ratio approach, segmental scalars for each channel ($\lambda_{b,i}^{AP}$ and $\lambda_{b,i}^{SI}$) were calculated according to Equation 9. As above, all energies in this study were estimated within a 500-sample moving window with 50% overlap. The scalars for the A-P and S-I channels ($\Lambda^{AP}$ and $\Lambda^{SI}$) were then estimated according to Equation 10. Rows 2-4 of the table in FIG. 6 document the effect of these scalar estimates on false positive reduction metrics.

Figure 6:
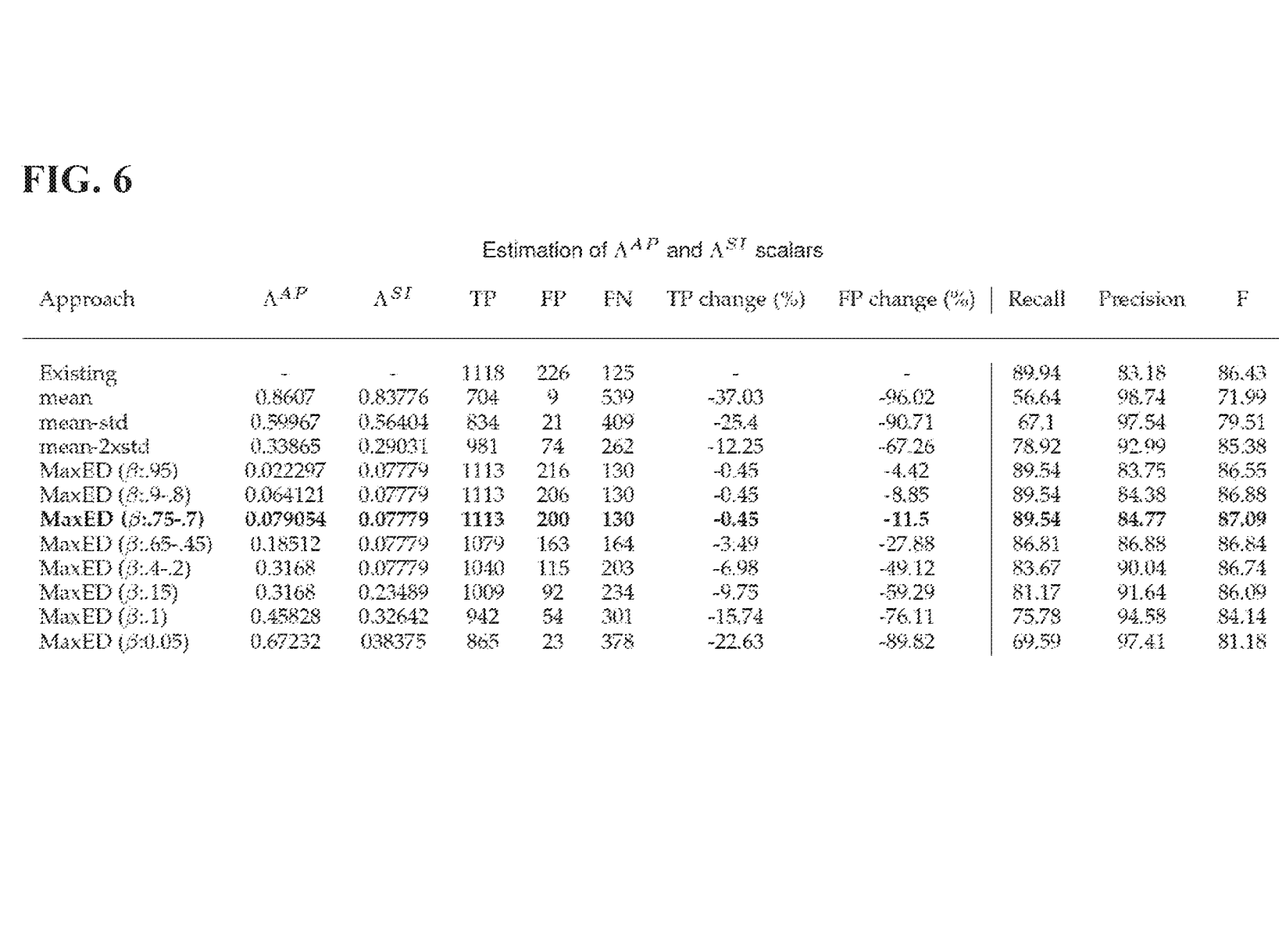
FIG. 6 is a table showing estimation of the scalars $A^{AP}$ and $A^{SI}$ in the experimental example disclosed herein.
Figure 7:
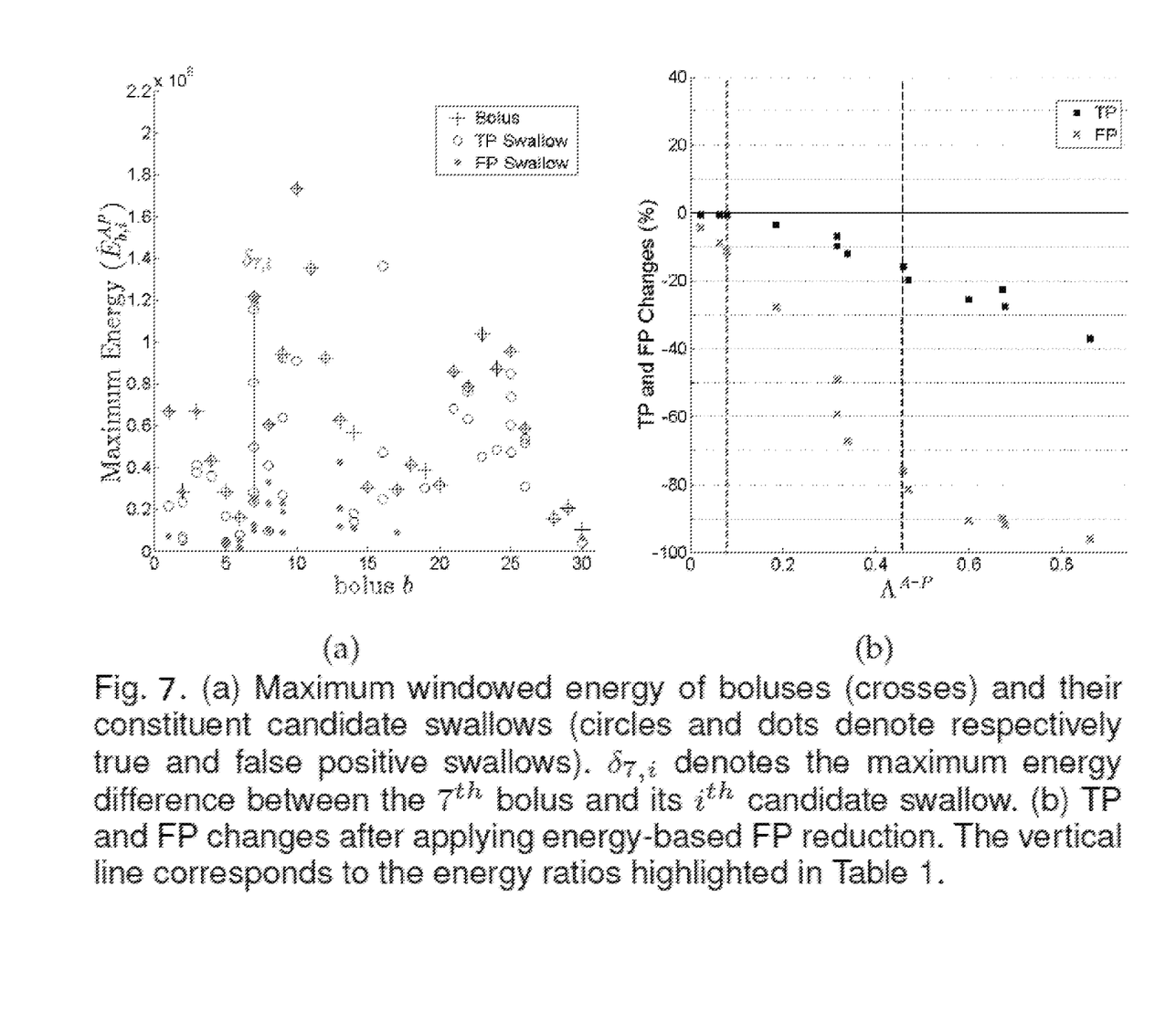
FIG. 7a is a graph showing maximum windowed energy of boluses (crosses) and their constituent candidate swallows in the experimental example disclosed herein.
FIG. 7b is a graph showing true positive (TP) and false positive (FP) changes after applying energy-based FP reduction in the experimental example disclosed herein.

FIG. 7a portrays the maximum energy of 30 randomly selected boluses (crosses), and their TP (open circles) and FP (dots) swallow segments. As shown in the figure, FP segments generally have lower maximum windowed energy than TP segments. Therefore, the scalar $\Lambda^{AP}$ was estimated by the energy difference approach in Equations 11-13, with the scalar $\Lambda^{AP}$ set as the energy ratio of swallow segment i' within bolus b': $\Lambda^{AP} = \lambda_{b',i'}^{AP}$. $\Lambda^{SI}$ was estimated by following the same procedure for the S-I axis. FIG. 6 summarizes 5 different estimations of these scalars.

FIG. 7*b* portrays FP and TP changes for different values of scalar $\Lambda^{AP}$. The vertical line delineates the scalars ($\Lambda^{AP}$=0.079, $\Lambda^{SI}$=0.078) that yielded the highest harmonic average, decreasing false positives by 11.5% with minimal change to the true positives.

To further reduce false positives, only candidates whose range exceeded that of the noise floor were accepted. This algorithm first computes the amplitude histogram of the bolus signal. The axial thresholds were then determined according to Equation 14. The noise signal range was re-estimated each time a swallow was detected and "removed" from the bolus.

Figure 8:
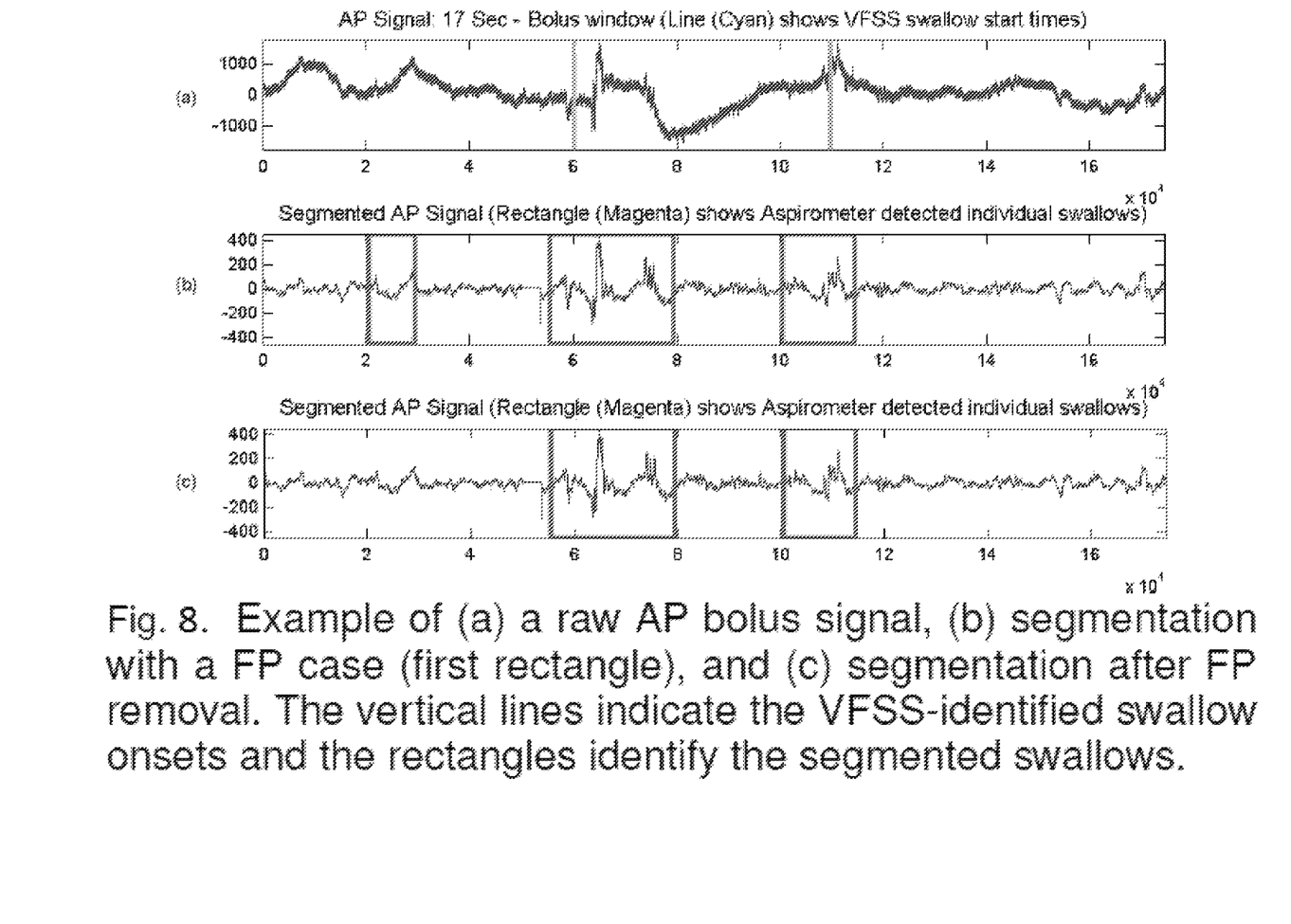
FIG. 8a is a graph showing a raw A-P bolus signal in the experimental example disclosed herein. The vertical lines indicate the VFSS-identified swallow onsets.
FIG. 8b is a graph showing segmentation with a FP case (first rectangle) in the experimental example disclosed herein. The rectangles identify the segmented swallows.
FIG. 8c is a graph showing segmentation after FP removal in the experimental example disclosed herein. The rectangles identify the segmented swallows.

The optimum values for $\alpha^{AP}$ and $\alpha^{SI}$ were estimated according to Equations 15 and 16. $\alpha^{AP*}$=7 and $\alpha^{SI*}$=4 led to a 74% FP reduction with only a 12% decrease in TP cases. FIG. 8 exemplifies a case where a FP swallow segment was removed after the application of this noise-floor FP reduction algorithm. The energy and noise-floor false positive reduction methods were applied in parallel on segmented, preprocessed data.

Only candidate segments that were identified as valid by at least one of the two FP reduction methods were admitted. If the loss of TPs was capped at 20%, the proposed methods led to a dramatic reduction in FPs (−85.4%) while sacrificing only 15.1% of TPs ($\Lambda^{AP}$=0.458, $\Lambda^{SI}$=0.326, $\alpha^{AP*}$=7, and $\alpha^{SI*}$=4).

In conclusion, the combined effect of the proposed energy and noise-floor methods was a definitive decrease in the number of false positives post-segmentation. The balance between FP reduction and loss of TPs can be fine-tuned according to the specific accelerometric application by tuning the axial thresholds.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of swallowing impairment detection, the method comprising:
    subjecting swallowing segments and non-swallowing segments of vibrational data to processing by a processing module, the processing selected from the group consisting of adaptive trimming, false positive reduction, and a combination thereof, and the vibrational data (i) represents swallowing activity, (ii) is from a sensor positioned externally on a throat of a patient and operatively connected to the processing module, and (iii) is associated with at least one axis selected from the group consisting of an anterior-posterior axis and a superior-inferior axis;
    classifying the swallowing segments and the non-swallowing segments as normal swallowing or a possible swallowing impairment after the processing of the swallowing and non-swallowing segments, and the processing module performs the classifying; and
    at least one selected from the group consisting of:
    (1) the method further comprising generating an output representing the classification, and the processing module generates the output;
    (2) wherein the possible swallowing impairment comprises at least one of a swallowing safety impairment or a swallowing efficiency impairment; and
    (3) wherein the possible swallowing impairment comprises penetration or aspiration, and the processing module further classifies the swallowing activity as indicative of one of a safe event or an unsafe event,
    wherein the processing comprises the adaptive trimming for each of the at least one axis, the adaptive trimming comprising forming trimmed segments from the swallowing segments and the non-swallowing segments, each of the trimmed segments from the swallowing segments comprises a portion of the respective segment corresponding to physiological vibrations associated with swallowing and exclude a portion of the respective segment corresponding to pre-swallow and post-swallow signal fluctuations; and
    wherein the adaptive trimming comprises, for each of the at least one axis:
    using kernel density estimation to obtain probability distributions for the swallowing segments and the non-swallowing segments, and
    determining an energy threshold based at least partially on the probability distributions, and
    the excluded portion is identified based on an energy difference of the excluded portion falling below the energy threshold.

2. The method of claim 1 comprising setting a probability cut-off for the probability distributions to adjust an extent of the adaptive trimming.

3. The method of claim 1 wherein the processing comprises the false positive reduction selected from the group consisting of energy-based false positive reduction, noise floor-based false positive reduction, and a combination thereof.

4. The method of claim 3 wherein the processing comprises the energy-based false positive reduction, and the energy-based false positive reduction comprises determining, for each of the least one axis, an axial energy-based bolus-specific threshold and discarding the swallowing segments having a maximum energy value less than the respective bolus-specific threshold.

5. The method of claim 3 wherein the processing comprises the noise floor-based false positive reduction, and the noise floor-based false positive reduction comprises generating an amplitude histogram of the vibrational data, using the amplitude histogram to determine an axial threshold for each of the at least one axis, and discarding the swallowing segments having a noise range greater than the respective axial threshold.

6. The method of claim 3 comprising adjusting an axial threshold to control a balance between removal of false positives and loss of true positives.

7. The method of claim 1 wherein the processing module receives the vibrational data from the sensor and automatically forms the swallowing segments and the non-swallowing segments from the vibrational data.

8. The method of claim 1 wherein the sensor is selected from the group consisting of a single-axis accelerometer and a dual-axis accelerometer.

9. An apparatus for quantifying swallowing function, the apparatus comprising:
    a sensor configured to be positioned on a throat of a patient and acquire vibrational data representing swallowing activity and associated with at least one axis selected from the group consisting of an anterior-posterior axis and a superior-inferior axis; and a processing module operatively connected to the sensor and configured to subject swallowing segments and non-swallowing segments of the vibrational data to processing selected from the group consisting of adaptive trimming, false positive reduction, and a combination thereof, wherein the processing comprises the adaptive trimming for each of the at least one axis, the adaptive trimming comprising forming trimmed segments from the swallowing segments and the non-swallowing segments, each of the trimmed segments from the swallowing segments comprises a portion of the respective segment corresponding to physiological vibrations associated with swallowing and exclude a portion of the respective segment corresponding to pre-swallow and post-swallow signal fluctuations; and wherein the adaptive trimming comprises, for each of the at least one axis:

using kernel density estimation to obtain probability distributions for the swallowing segments and the non-swallowing segments, and determining an energy threshold based at least partially on the probability distributions, and the excluded portion is identified based on an energy difference of the excluded portion falling below the energy threshold.

10. The apparatus of claim 9, comprising an output component selected from a display, a speaker, and a combination thereof, the processing module configured to classify the swallowing segments and the non-swallowing segments as normal swallowing or a possible swallowing impairment after the processing of the swallowing segments and the non-swallowing segments, the processing module configured to use the output component to indicate the classification visually and/or audibly.

11. The apparatus of claim 9 wherein the processing module is operatively connected to the sensor by at least one of a wired connection or a wireless connection.

12. The apparatus of claim 9 wherein the processing module is configured to receive the vibrational data from the sensor and automatically form the swallowing segments and the non-swallowing segments from the vibrational data.

13. A method of treating dysphagia in a patient, the method comprising:

positioning a sensor externally on a throat of the patient, the sensor acquiring vibrational data representing swallowing activity and associated with at least one axis selected from the group consisting of an anterior-posterior axis and a superior-inferior axis, the sensor operatively connected to a processing module subjecting swallowing segments and non-swallowing segments of the vibrational data to processing selected from the group consisting of adaptive trimming, false positive reduction, and a combination thereof, the processing module generating an output indicative of a classification of the vibrational data, wherein the processing comprises the adaptive trimming for each of the at least one axis, the adaptive trimming comprising forming trimmed segments from the swallowing segments and the non-swallowing segments, each of the trimmed segments from the swallowing segments comprises a portion of the respective segment corresponding to physiological vibrations associated with swallowing and exclude a portion of the respective segment corresponding to pre-swallow and post-swallow signal fluctuations; and wherein the adaptive trimming comprises, for each of the at least one axis:

using kernel density estimation to obtain probability distributions for the swallowing segments and the non-swallowing segments, and determining an energy threshold based at least partially on the probability distributions, and the excluded portion is identified based on an energy difference of the excluded portion falling below the energy threshold; and adjusting a feeding administered to the patient based on the classification.

14. The method of claim 13 wherein the adjusting of the feeding is selected from the group consisting of changing a consistency of the feeding, changing a type of food in the feeding, changing a size of a portion of the feeding administered to the patient, changing a frequency at which portions of the feeding are administered to the patient, and combinations thereof.

* * * * *